Figure 1:
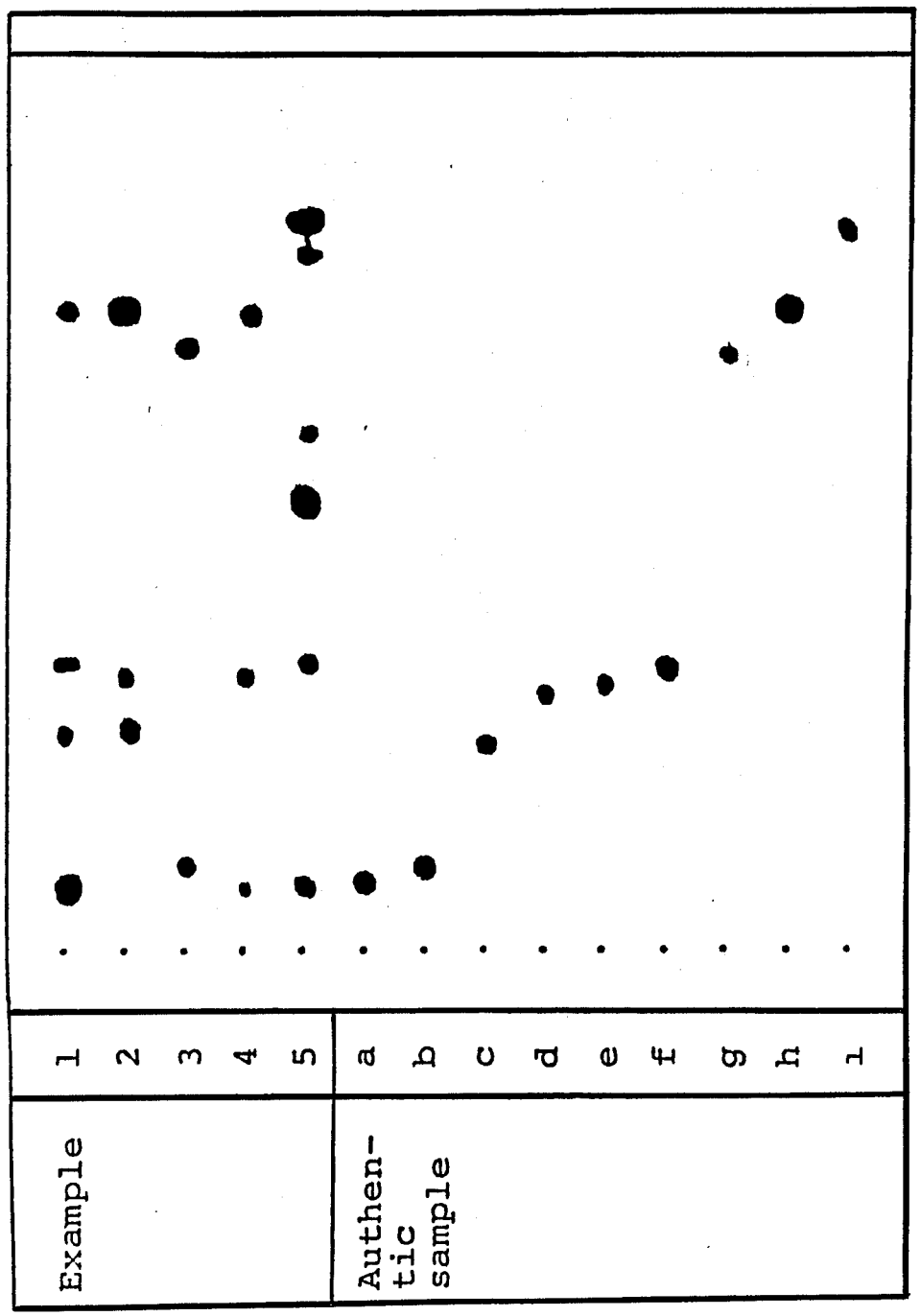

United States Patent [19]

Yamamoto et al.

[11] Patent Number: 4,937,195

[45] Date of Patent: * Jun. 26, 1990

[54] TISSUE CULTURE OF LICHENS

[75] Inventors: Yoshikazu Yamamoto, Neyagawa; Ryuzo Mizuguchi, Yawata; Yasuyuki Yamada, Uji, all of Japan

[73] Assignee: Nippon Paint Co., Ltd., Osaka, Japan

[*] Notice: The portion of the term of this patent subsequent to Aug. 20, 2002 has been disclaimed.

[21] Appl. No.: 867,589

[22] Filed: May 27, 1986

Related U.S. Application Data

[63] Continuation of Ser. No. 541,727, Oct. 13, 1983, abandoned, and a continuation-in-part of Ser. No. 431,096, Sep. 30, 1982, Pat. No. 4,536,474.

[30] Foreign Application Priority Data

| Sep. 30, 1981 | [JP] | Japan | 57-156765 |
| Oct. 27, 1981 | [JP] | Japan | 57-172605 |
| Oct. 27, 1981 | [JP] | Japan | 57-172606 |
| Mar. 4, 1983 | [JP] | Japan | 58-36388 |

[51] Int. Cl.$^5$ ............ C12N 1/00; C12N 1/14; C12N 1/12; C12R 1/645; C12R 1/89

[52] U.S. Cl. ............ 435/243; 435/254; 435/257; 435/911; 435/946

[58] Field of Search ............ 47/1.4, 5.8; 435/174–182, 911, 946, 240, 243, 254, 257, 317

[56] References Cited

U.S. PATENT DOCUMENTS 4,148,689 4/1979 Hino et al. .................. 435/182

OTHER PUBLICATIONS

Ahmadjian, U., *Science*, vol. 151, pp. 199–201, 1966.
Hale, M., *The Biology of Lichens*, (eds. Barringtone & Willis, AJ) Edward Arnold Publishers, pp. 103–119, 1967.
Ahmadjian, U., *The Lichen Symbiosis*, Blaisdell Publ., pp. 92–93, 1967.
Singleton, P. et al., *Dictionary of Microbiology*, pp. 223–225, 1978.
Brodelius, FEBS Letters, vol. 122(2), pp. 312–316, 180.
Asahina, Y, et al, *Chemistry of Lichen Substances*, pp. 3–9, 1954.
Reinhart, J., Plant Cell and Tissue Culture (Springer-Verlag Publishers), pp. 4–7, 1982.

*Primary Examiner*—Jayme A. Huleatt
*Attorney, Agent, or Firm*—Wenderoth, Lind & Ponack

[57] ABSTRACT

An undifferentiated symbiotic combination of lichen flora induced from a tissue of lichen flora and having a capability of producing any lichenous substance.

3 Claims, 1 Drawing Sheet

TISSUE CULTURE OF LICHENS

This is a Rule 62 Continuation of Ser. No. 541,727, filed Oct. 13, 1983, now abandoned, which in turn is a continuation-in-part application of our copending application Ser. No. 431,096 filed on Sept. 30, 1982, now U.S. Pat. No. 4,536,474.

The present invention relates to an undifferentiated symbiont induced from the tissue of lichen flora, and its production.

Lichens are the plants which are characterized by a symbiont (symbiotic combination) consisting of fungi and algae, and hence occupy an unusual position in botany. From microscopic observation, lichens differentiate varieties of tissues including cortex (a tissue covering and protecting thallus and consisting of gathered and adhered hyphae), algal layer (a tissue in which algae in thallus are surrounded and supported by hyphae), medulla (a basic tissue of thallus consisting of loosely entangled hyphae) and rhizine (a tissue projecting on the under-side surface and sticking the thallus on a carrier), which are the structural characteristics of lichens. (But, in some cases, the under-side surface of thallus do not have rhizine.)

Lichenous substances, which are the metabolic products of lichens, are different from the most of the higher or lower plant substances and belong to a special, limited chemical division. According to Asahina (Asahina and Shibata, "Chemistry of Lichenous Substances", Kawade Shobo, 1948), the lichenous substances may be classified into the following groups:

A. Aliphatic lichenous substances
  Group 1. Acids
    (a) Monobasic lactone-acids
    (b) Dibasic acids
    (c) Tribasic acids
  Group 2. Neutral compounds which show Liebermann's reaction (Zeorin compounds)
  Group 3. Polyhydric alcohols
B. Aromatic lichenous substances
  Group 1. Pulvic acid derivatives
  Group 2. Depsides
    (a) Orcin compounds
    (b) Orcin- -orcin mixed compounds
    (c) -Oricin compounds
  Group 3. Depsidones
    (a) Orcin compounds
    (b) -Orcin compounds
  Group 4. Quinones
    (a) Oxyanthraquinones
    (b) Phenanthrene quinones
  Group 5. Xanthone derivatives
  Group 6. Diphenyleneoxide derivatives
  Group 7. Nitrogen-containing compounds (Diketopiperadine derivatives)
C. Carbohydrates
  Group 1. Polysaccharides More precisely, the following compounds are included as representative of the lichenous substances:

I. DEPSIDONES:

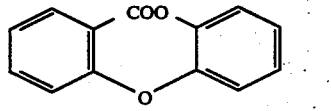

| Compound | Structure |
|---|---|
| Variolaric acid | 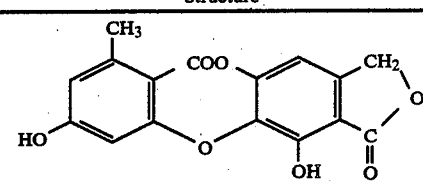 |
| Norstictic acid | 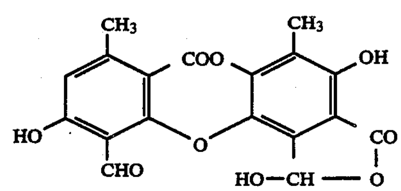 |
| Pannarin | 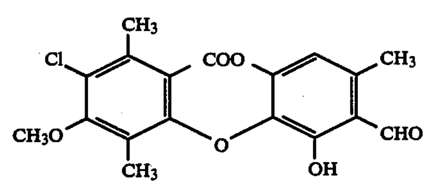 |
| Physodalic acid | 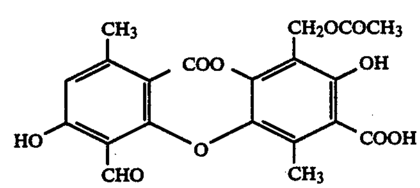 |

-continued
I. DEPSIDONES:
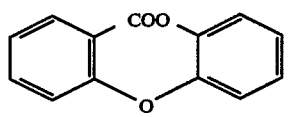
| Compound | Structure |
|---|---|
| Physodic acid | 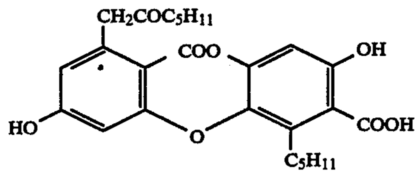 |
| Psoromic acid | 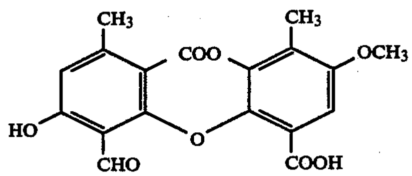 |
| Fumaroprotocetraric acid | 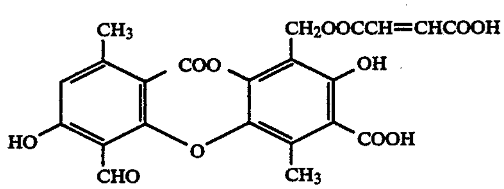 |
| Lobaric acid | 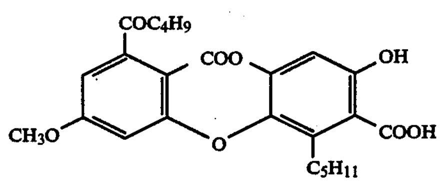 |
| α-Collatolic acid | 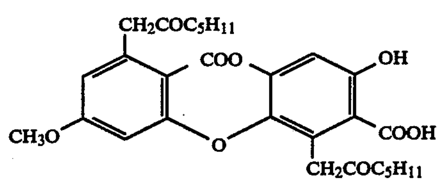 |
| Salazinic acid | 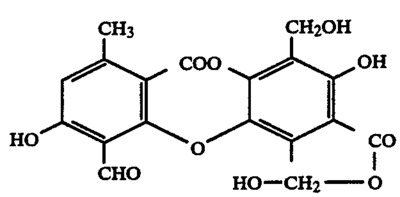 |
| Stictic acid | 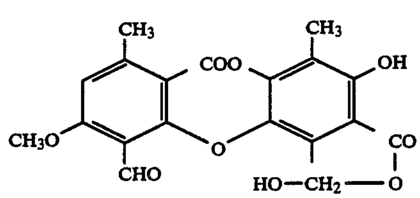 |

-continued
I. DEPSIDONES:
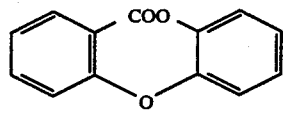
| Compound | Structure |
| --- | --- |
| Alectronic acid | (structure shown) |
| Protocetraric acid | (structure shown) |
II. DEPSIDES
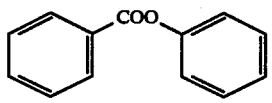
| Compound | Structure |
| --- | --- |
| Hypotamnolic acid | (structure shown) |
| Thamnolic acid | (structure shown) |
| Boninic acid | (structure shown) |
| Homosekikanic acid | (structure shown) |
| Barbatic acid | (structure shown) |

-continued
II. DEPSIDES

| Compound | Structure |
|---|---|
| Balbatolic acid | 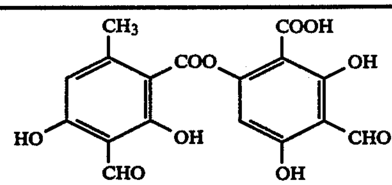 |
| Microphyllic acid | 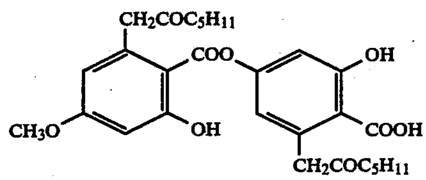 |
| Sphaerophorin | 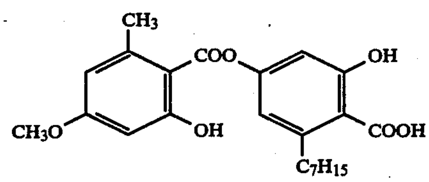 |
| Sekikaic acid | 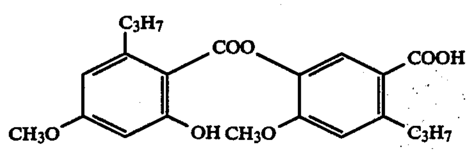 |
| Diffractaic acid | 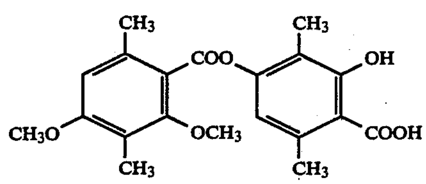 |
| Atranorin | 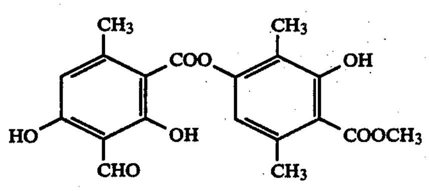 |
| Lecanoric acid | 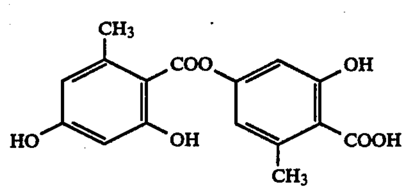 |
| Anziaic acid | 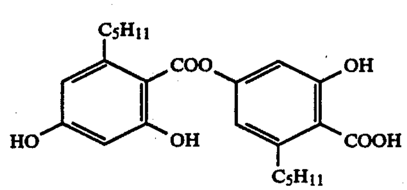 |

II. DEPSIDES
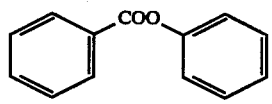
| Compound | Structure |
|---|---|
| Evernic acid | 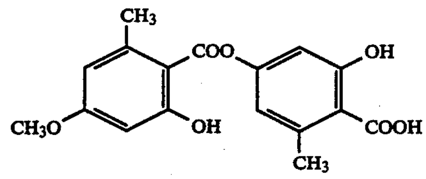 |
| Obtusatic acid | 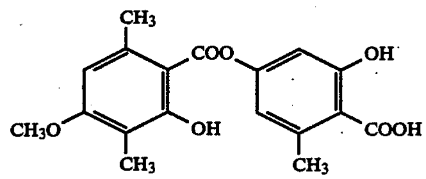 |
| Olivetoric acid | 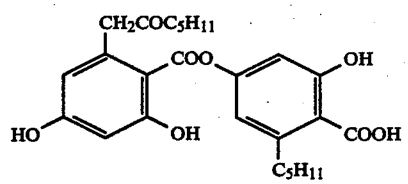 |
| Baeomycesic acid | 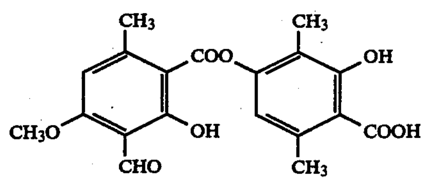 |
| Perlatolic acid | 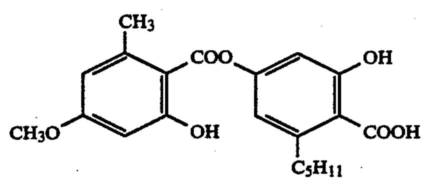 |
| Tenniorin | 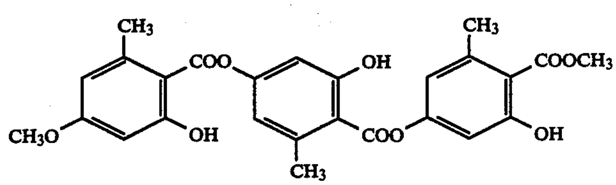 |
| Umbilicaric acid | 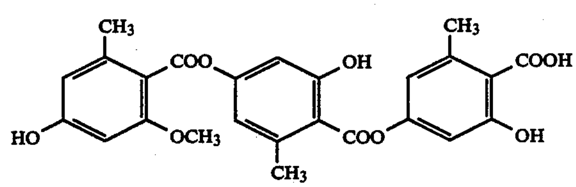 |

| III. DIPHENYLENEOXIDES | |
|---|---|
| 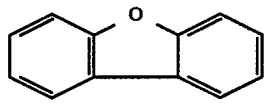 | |
| Compound | Structure |
| Strepcilin | 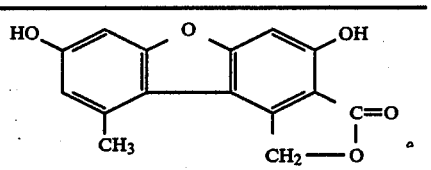 |
| Didymic acid | 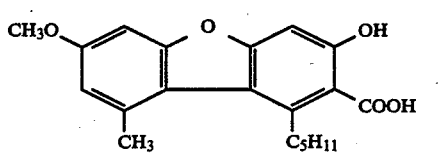 |
| III. DIPHENYLENEOXIDES -continued | |
|---|---|
| 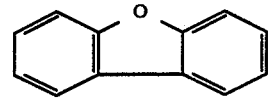 | |
| Compound | Structure |
| Usnic acid | 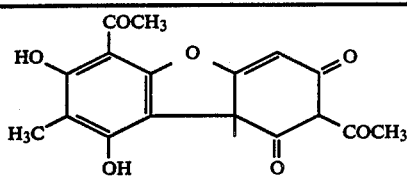 |
| IV. VULPINIC ACIDS | |
|---|---|
| 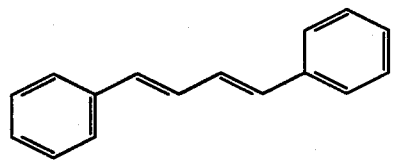 | |
| Compound | Structure |
| Calycine | 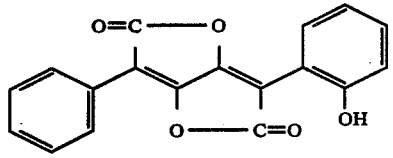 |
| Pynastolinic acid | 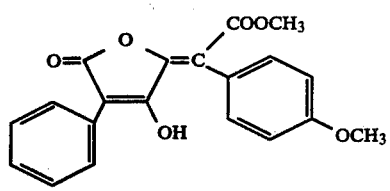 |
| Rhyzocarpinic acid | 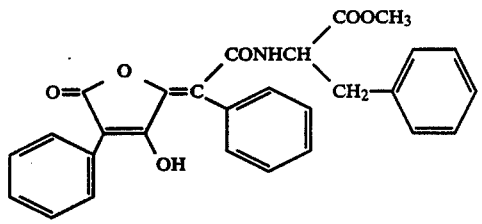 |
| Vulpinic acid (Pulvic acid methyl ester) | 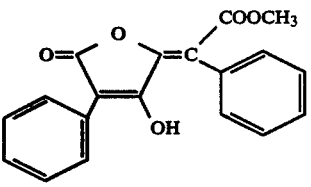 |

V. ANTHRAQUINONES

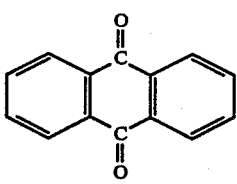

| Compound | Structure |
|---|---|
| Rodocradonic acid | HO, OH, HOH₂C, COOCH₃, HO, OH (anthraquinone core) |
| Endcrotin | HO, OH, COOH, HO, CH₃ (anthraquinone core) |
| Pariethine | HO, OH, CH₃O, CH₃ (anthraquinone core) |

VI. PHENANTHRENEQUINONES

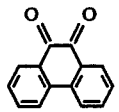

| Compound | Structure |
|---|---|
| Telephoric acid | OH, HO, CH=CH—CH=CH—COOH, COOH (phenanthrenequinone core) |

VII. FATTY ACIDS

| Compound | Structure |
|---|---|
| Rangiformic acid | $\left.\begin{array}{l}CH_2COOH\\CHCOOH\\CHCOOH\\(CH_2)_{13}CH_3\end{array}\right\}CH_2$ |

VII. FATTY ACIDS

| Compound | Structure |
|---|---|
| Caperatic acid | $\left.\begin{array}{l}CH_2COOH\\C(OH)COOH\\CHCOOH\\(CH_2)_{13}CH_3\end{array}\right\}-CH_2-$ |

VIII. TRITERPENES

| Compound | Structure |
|---|---|
| Zeorin | (triterpene structure with HO, OH, OH groups) |
| Ursolic acid | (triterpene structure with HO, COOH groups) |

IX. TETRONIC ACIDS

| Compound | Structure |
|---|---|
| Protolichesterinic acid | $CH_3\text{---}(CH_2)_{11}\text{---}CH_2\text{---}CH$, $C=O$, $CH\text{---}CH=CH_2$, $HOOC$ |

X. XANTHONES (xanthone core structure)

| Compound | Structure |
|---|---|
| Thiophanic acid | CH₃, OH, Cl, CH₃O, OH, Cl (xanthone core) |

As to the physiological significance of the lichenous substances, it is considered that the lichenous substances may be helpful in protecting lichens from the attack of microorganisms or the bite of small animals because the growth rate growing of lichens is very slow, or that the lichenous substances are useful for protecting lichens from ultraviolet rays because lichens grow in the sun's rays differently from other fungi. Therefore, the lichenous substances have been employed in various uses such as dyestuffs, antibiotics, perfumes, etc. on the basis of the above functions.

Since the growth of lichens is very slow and is affected by natural environment such as season, climate, temperature or latitude, and artificial conditions such as sulfurous acid gas or smoke, natural cultivation of lichens is very difficult and has never been successful. Collection of wild lichens is also difficult because much skill is required for identification of lichens due to the fact that there are numerous lichens which resemble closely each other in appearance but different in composition.

It was proposed (Yoshimura, "Lichen Flora of Japan in Color", p. 319, Hoikusha) that lichenous fungi be separated from lichenous algae and be cultured for producing the lichenous substances. However, in this method, the lichenous substances are not produced in some cases due to lack of effects obtainable by symbiosis.

Recently, the tissue culture of higher plants has been studied as a technique for producing plant substances. Since a plant tissue under culture grows much more rapidly than a natural plant, the growth of which takes months or years, the tissue culture enables the production of plant substances in a shorter period and the prearranged production in on an industrial scale is possible without being affected by climate or needing man's power for harvesting, in contrast to natural growing. However, success in tissue culture of lichens has never been reported, although its study has been continued.

According to the invention, it has now been discovered that the tissue culture of lichens can be carried out successfully by inducing an undifferentiated symbiont from the lichenous tissue and culturing said undifferentiated symbiont in an appropriate medium, and that the symbiotic effects are fully used to activate the growth of the symbiont so that the lichenous substances are produced in an excellent yield.

Ordinary culture processes have been attempted in order to increase lichens artificially as mentioned above. However, in the conventional processes, importance has been attached to fungus cells and efforts have been continuously put into increasing them. In contrast to the conventional processes, the inventors have attached importance to the relation between fungus and alga. As a result, the inventors have succeeded in inducing the coexistent state of fungus and alga as an undifferentiated symbiont and in establishing an industrial process which allows rapid and stationary production of the lichenous substances by culturing said undifferentiated symbiont. Accordingly, the main characteristic of the invention resides in culture of the undifferentiated symbiont as a novel technical concept, and this enables the rapid and stationary production of the lichenous substances as an industrial scale. The undifferentiated symbiont itself is novel to the best of knowledge of the present inventors and culture of the undifferentiated symbiont has never been attempted. Needless to say, it has not been known that the lichenous substances can be produced favorably by culturing the undifferentiated symbionts.

As it can be clearly seen from Examples described hereinbelow, the present invention is universally applicable to various lichens belonging to a great number of families including Teloschistaceae, Physciaceae, Buelliaceae, Usneaceae, Aziaceae, Parmeliaceae, Candelariaceae, Lecanoraceae, Pertusariaceae, Acaropsoraceae, Imbilicariaceae, Cladoniaceae, Baeomycetaceae, Stereocaulaceae, Lecideaceae, Gyalectaceae, Asterothyriaceae, Stictaceae, Peltigeraceae, Pannariaceae, Coccocarpiaceae, Placynthiaceae, Heppiaceae, Collemataceae, Lichinaceae, Graphidaceae, Thelotremataceae, Diploschistaceae, Verrucariaceae, Pyrenulaceae, Strigulaceae, Sphaerophoraceae, Calidiaceae, Cypheliaceae, Lecanactidaceae, Opegraphaceae, Arthopyreniaceae, Arthoniaceae, Dictyonemaataceae, Clavariaceae, Agaricaceae and so on.

In the above and following description, the term "undifferentiated symbiont" means a system consisting of at least one alga cell and at least one fungus cell, which exhibits symbiotic effects between alga and fungus, but has not differentiated i.e. has retained the structural characteristics in lichens.

The term "symbiotic effects" means certain synergistic effects acting between alga and fungus and activating growth of alga and fungus as well as production of metabolites. It is considered that these effects are caused by transfer of physiologically active trace substances including nutrients.

The undifferentiated symbionts of lichens used in the invention are obtained by inducing from a lichenous plant which is used as the starting material. A practical procedure for induction of the undifferentiated symbionts is illustrated, taking *Usnea rubescens* (Usneaceae, Lecanorales) by way of example, in the followings:

Thallus of *Usnea rubescens* is washed sufficiently with deionized sterile water and cut into a small piece having an appropriate size with a sterile scalpel. The piece must include both alga and fungus. The piece is placed on a suitable culture medium such as a solid medium, for example, Murashige and Skoog's medium, and incubated at a constant temperature, preferably between 0° C. and 40° C. and ordinarily in light.

After about 3 weeks of culture, there are formed undifferentiated symbionts, which are transplanted sterilely on a fresh culture medium having appropriate composition and incubated at a constant temperature between 0° C. and 40° C., preferably between 20° C. and 35° C., and ordinarily in light. In a preferred emobodiment, the undifferentiated symbionts obtained above are suspended in a liquid culture medium and subjected to so-called liquid culture such as stationary culture, shaking culture, agitation culture or aeration culture, because the liquid culture is suitable for production on an industrial scale and symbiotic effects are more remarkable than solid culture due to quick transfer of material between alga and fungus in the symbiont.

The medium for culture of undifferentiated symbiont may be any natural or synthetic, organic or inorganic culture medium such as, for example, conventional inorganic synthetic culture medium containing organic substances such as nutrients, carbon sources and other natural extract substances within the limit of avoiding adverse affection of the symbiotic effects. Typical examples of inorganic synthetic culture medium are White's culture medium, Hildebrand's medium, Linsmaier-Skoog's medium, Murashige-Skoog's medium, etc.

Said nutrients may be vitamins such as thiamine hydrochloride, pyridoxine hydrochloride and nicotic acid, amino acids such as glycine and asparagine, hexahydric alcohols such as inositol and sorbitol, etc. Examples of said carbon sources include carbohydrates (e.g. sucrose, glucose, maltose), organic acids (e.g. acetic acid) and alcohols (e.g. methanol, glycerol). Said natural extract substances can be casein hydrolyzate, coconut milk, yeast extract, malt extract, etc. They can be used solely or in combination.

Photopic culture in the invention may be carried out by placing the culture in light not more than 10,000 lux, ordinarily 500–10,000 lux. As the light source, sun light, a fluorescent lamp, an incandescent lamp, a mercury lamp or the like can be used. Ordinarily, algae do not grow without application of light. The application of light may be continuous or intermittent with a period of several hours.

When the culture of symbiont is carried out in a $CO_2$-enriched atmosphere, the symbiotic effects can be increased and the growth of symbiont is activated. Thus, it is preferable to supply continuously $CO_2$-containing air in a culturing tank. Suitable concentration of carbon dioxide gas in the air is from 0.1 to 5% (by volume), preferably from 0.5 to 2%, in order to activate the growth of the undifferentiated symbiont.

The lichenous substances may be isolated from cultured undifferentiated symbiont by any convenient or conventional method. One of practical procedures for isolating lichenous substances by solvent extraction is illustrated, taking Usnea rubcscens by way of example, in the followings:

The cultured undifferentiated symbionts are collected by filtration of culture medium and dried at 60° C. for 24 hours or at 100° C. for 3 hours in order to remove water. Then, the dried symbionts are extracted with acetone by means of Soxhelet extraction, digestion or merceration. The acetone may be replaced by other polar solvents (e.g. methanol, ethanol). Acetone extract is concentrated in order to remove acetone. The concentrate is partitioned between water and ethyl acetate. The ethyl acetate may be replaced by other organic solvents (e.g. chloroform, methylene dichloride, n-hexane, ethyl ether, benzene, methyl acetate, n-pentane, cyclohexane, petroleum ether). Then, the ethyl acetate layer is separated from aqueous layer and concentrated by evaporating ethyl acetate. The concentrate is subjected to column chromatography or thin-layer chromatography to give usnic acid as a desired lichenous substance.

The usnic acid obtained above has a melting point about 203° C. and agrees with the commercially available usnic acid in thin-layer chromatography using silica gel G with various solvent system such as hexane/ethyl/formic acid=130/80/20, hexane/ethyl acetate/formic acid=50/40/7, benzene/dioxane/formic acid=90/45/4 (all ratios being given by volume). Also, it agrees with the commercial one in infrared spectrum and nuclear magnetic spectrum. The obtained usnic acid is identified by the above analytical methods.

Still, said undifferentiated symbionts may be obtained and used in any immobilized state. It was known that various living cells can be combined to, adsorbed on or trapped in carriers such as high molecular compounds. However, in the known technique, only one kind of bacterial cell or plant or animal cells was used. Thus, it has never been attempted to immobilize the complex system of different cells, especially a symbiont. The inventors have attached importance to the fact that the lichens are symbionts of algae and fungi, and have found that the undifferentiated symbionts are easily dispersed in media as compared with the naturally occurring differentiated symbionts of lichens, and as a result, have succeeded in obtaining industrially useful immobilized plant tissue by coagulating said undifferentiated symbionts.

Immobilization may be effected by any convenient method such as the carrier-bonding method, trapping method or crosslinking method, and preferably such method is selected according to purpose of usage and kind of lichens to be immobilized. For instance, when the symbionts are intended to immobilize a living catalyst, immobilization is preferably effected under mild conditions in which symbiotic effects between alga and fungus are maintained, because enzymatic activity in immobilized symbionts must be stabilized.

The carrier-bonding method includes the covalent bonding method in which carrier and undifferentiated symbionts are covalently bonded together, ionic bonding method in which undifferentiated symbionts are bonded by ionic reaction to the carrier having an ion-exchange group, physically adsorbing method, and biologically adsorbing method, etc., among which the most preferred is the ionic bonding method. The carrier is preferably insoluble as well as porous and has a suitable pore size for capturing the undifferentiated symbionts. Suitable carriers include natural high molecular carriers (such as polysaccharide including agarose, cellulose, insoluble protein such as collagen, gelatin), synthetic high molecular carrier (such as vinyl resin, acryl resin, polyester resin, polyamide resin, epoxy resin, polyether resin, urethane resin), inorganic carrier (such as alumina, glass, avalite, bone dust, acid clay), and these may be used solely or in admixture.

The trapping method includes a method in which undifferentiated symbionts of lichens are trapped in a grid of natural high molecular compound such as carrageenan or synthetic high molecular compound such as polyacrylamide gel, which are prepared by polymerization, and a method in which said symbionts are trapped in microcupsules of semipermeable membrane or hollow fiber. The trapping method is advantageous for immobilizing undifferentiated symbionts of lichens because the undifferentiated symbionts are immobilized without chemical modification and hence marring of enzymatic activity on symbiotic form is minimized. Preferably, the carrier has a net-like structure with a suitable mesh size for capturing the undifferentiated symbionts of lichens. Such carrier includes natural high molecular carrier (such as alginic acid salt, carrageenan, starch, agar, cellulose, albumin), synthetic high molecular carrier (such as polyacrylamide, photo-crosslinking synthetic resin, radiation-polymerizing synthetic resin).

The crosslinking method is a method in which the undifferentiated symbionts of lichens are immobilized by combining the undifferentiated symbionts with each other using bifunctional reagents such as glutaraldehyde or other multifunctional reagents. Said bifunctional reagents include dialdehydes such as glutaraldehyde, imidoesters such as dimethyl adipinimidate, diethyl-d, 3'-dithiolbispropionimidate, triazines such as 1,3-dichloro-5-methoxytriazine, 1,3,5-trichlorotriazine, diisocyanates such as tolylenediisocyanate.

The carrier-bonding method, trapping method and crosslinking method are solely used in general, but may be used in combination depending upon the usage or kind of lichens. For example, the symbionts may be adsorbed on collagen and then crosslinked with glutaraldehyde.

The immobilized lichenous tissues according to the invention are useful as a catalyst for preparing or converting primary or secondary metabolites, deodorizing agents, adsorbents for heavy metal ion, bioelectrodes and carriers for perfume, fertilizer or agricultural chemicals. In addition, industrial production of specific products may be realized by culturing undifferentiated symbionts of lichens which are trapped in polymer particles and which have a high capacity for producing said specific product together with other symbionts in the same culture tank.

This invention also relates to a block of cells of lichen flora having no material contamination with any other bacterium or fungus, and a method for obtaining such cell blocks of high purity.

Various attempts have been made to isolate fungus and/or algal cells of lichen flora in a highly pure state, i.e. without any material contamination of other bacteria or fungi. However, those attempts have always been accompanied by difficulties. For instance, the rinsing of any tissue of lichen flora with an aqueous solution comprising any antibiotic agent so as to remove other bacteria and fungi attached to the tissue is sometimes applied. Since, however, the tissue of lichen flora is water-absorptive, the antibiotic agent is apt to be retained therein. In addition, both the fungus and algal cells of lichen flora are similar to the cells of other bacteria and fungi in the behavior to various antibiotic agents. Because of these reasons, the use of a high concentration of the antibiotic agent sufficient to kill other bacteria and fungi may simultaneously cause serious damage on the tissue of lichen flora. Collection of only the cells of lichen flora from any culture medium on which those cells were cultivated together with other bacteria or fungi has also been tried on occasion. Since, however, the growth of the cells of lichen flora is usually much slower than that of other bacteria or fungi, the efficient collection is practically impossible. In case of lichen flora of the kind of forming an apothecium, it may be possible to collect ascospores from the apothecium avoiding any contamination with other bacteria and fungi, and the use of the collected ascospores will accomplish enable to accomplish cultivation in a pure state. However, the collection of the ascospores requires extremely rare skill. Further, the growth of the collected ascospores is not necessarily smooth on cultivation. Furthermore, the formation of the apothecium is restricted not only in the kind of plant but also in the period of growth.

This invention makes possible to obtain a block of cells of lichen flora having no material contamination with any other bacterial or fungous cell by a simple operation comprising micronizing and filtration.

According to the invention, a block of cells of lichen flora having no material contamination with any other bacterial or fungus cell, the number of the cells in the block being at least two and the maximum size of the block being not more than 10 mm, can be obtained by micronizing at least a portion of the plant body of lichen flora having contamination with any other bacterium or fungus so as to leave at least one block of cells of lichen flora comprising at least two of the cells and having a maximum size of not more than 10 mm, subjecting the micronized product to filtration with at least one filter which can retain the said block and pass any other cell(s) of lichen flora and/or any other bacterium or fungus therethrough and collecting the said block retained on the filter. Advantageously, the cell block(s) obtained by this invention can grow quite rapidly on cultivation in comparison with a single fungus or algal cell.

Cultivation of a tissue of lichen flora has been frequently carried out. Generally, however, the cultivation was effected with the tissue of an appropriate size. Micronization of such tissue, particularly to such an extent as in this invention, prior to the cultivation has never been attempted. This is due the common consideration that the micronization may result in the break and death of the cells of lichen flora and be undesirable for the purpose of cultivation.

The term "maximum size" hereinabove used is intended to mean the maximum size when measured on various distances across the cell block.

The said method for obtaining the pure cell block of lichen flora is generally applicable to various lichens belonging to a great number of families as exemplified above.

A practical procedure for obtaining the pure cell block will be hereinafter illustrated taking Usnea rubescens (Usneaceae, Lecarnorales) as an example.

Thallus of Usnea rubescens is cut in optional size, and the resultant pieces are well washed with water. Then, the washed pieces are micronized by physical and/or chemical operations to obtain cell blocks' of small size. For micronization, there may be adopted any physical (i.e. mechanical) procedure using a mortar, a homogenizer, a knife, a microtome or the like. Micronization may be also achieved by any chemical procedure using a reagent cutting the intercellular bond such as cellulase (e.g. "Dricellase" manufactured by Kyowa Hokko; "Cellulase-Onozuka" manufactured by Kinki Yakult).

The resultant micronized product comprises monocellular bacteria or fungi, cells of Usnea rubescens, cell blocks of Usnea rubescens, etc. From such product, only the cell blocks of Usnea rubescens comprising at least two cells and having a maximum size of not more than 10 mm, preferably at least 10 cells and having a maximum size of not more than 1 mm. This size of the cell block is desirable for assured survival of the cell block and efficient elimination of other contaminating cells.

For collection of the said cell blocks, there are available the procedure using a manipulator, the procedure using a cell sorter, the procedure with centrifugation, etc., among which the procedure using at least one filter is the most recommendable in view of obtaining a large amount of the desired cell blocks by a simple operation within a short time. The filter may be made of any material which does not afford any unfavorable influence on the cell blocks such as nylon or stainless steel.

Usually, the micronized product as obtained above is first passed through a filter having a mesh size of not more than 1,000 microns, and the filtrate is then passed through a filter having a mesh size of not less than 10 microns. The cell blocks retained on the filter are collected, followed by washing with sterile water.

The cell blocks are placed on media suitable for growth and cultivated at a temperataure of 0 to 40° C. After about one month, the cell cultures are grown to such an extent as can be observed by naked eye. The cultivation may be effected while shaking or stirring or under a stationary condition. The media for cultivation may be prepared, for instance, by adding nutrient sources, carbon sources, organic sources (e.g. extracts of natural products), etc. to synthetic organic or inorganic media as basal media. Specific examples may be those as hereinabove exemplified.

When desired, the media for cultivation may contain any antibiotic agent so as to enhance the selection efficiency of the cell blocks of lichen flora or obtain the cell blocks consisting of fungus cells or algal cells only. For the purpose of obtaining the blocks of fungus cells, such an anti-algae agent as kanamycin (manufactured by Meiji Seika) or sorcilin (manufactured by Takeda Yakuhin) may be incorporated. For the purpose of obtaining the blocks of algal cells, such an anti-fungal agent as coatside (a benzimidazole compound; manufactured by Takeda Yakuhin) may be incorporated.

The invention will now be further illustrated by means of the following examples. Cultures of the undifferentiated symbionts as used in those examples are deposited at the Depository in the Technical Center belonging to Nippon Paint Co. Ltd. at Neyagawa-shi, Osaka-fu, Japan, and one of them is also deposited at American Type Cuture Center in the United States. Since a reliable method for preservation of the cultures in the state of rest has not been established, the cultures are kept in a living state. Thus, the living cultures, for instance, on slant agar media comprising malt extract (Difco) (2% w/v), yeast extract (Difco) (0.2% w/v) and agar (2% w/v) may be kept at 20° C. in a dark place and successively transplanted to the same media as above with intervals of every 2 months.

Part A:

EXAMPLE 1

A piece with a length of about 1 cm was cut from the thallus of Usnea rubescens (Usneaceae, Lecanorales) collected at Kyoto-shi, washed sufficiently with water and rinsed several times in sterile distilled water in a sterile cup-board. The obtained explant of lichen was placed aseptically on a synthetic agar culture medium. The medium consisted of Murashige and Skoog's inorganic salt formulation containing 0.1 ppm thiamine hydrochloride, 0.5 ppm pyridoxine hydrochloride, 0.5 ppm nicotic acid, 2 ppm glycine and 100 ppm inositol, adjusted at pH 6.0, to which was added 1.0% weight by volume of agar. The medium was used after being sterilized in a usual manner.

The explant was incubated at 25° C. in light of 2,000 lux. After about 3 weeks of culture, there were formed green-colored undifferentiated symbionts (deposited at the American Type Culture Collection under Accession No. ATCC 20654 and also at the Depository in the Technical Center belonging to Nippon Paint Co., Ltd. under Deposition No. NP L-29).

About 1 g (wet weight) of the undifferentiated symbionts obtained above was transplanted in 100 ml of a liquid culture medium excepting agar, and incubated at 25° C. in light of 2,000 lux on a shaker with a shaking velocity of 80 rpm. After a month of culture, the medium was filtered to give about 5 g (wet weight) of undifferentiated symbionts.

The symbionts were crushed in a mortar and extracted three times with acetone for 8 hours in a Soxhelet extractor. The obtained acetone extracts were combined, concentrated to about 50 ml and shaken with the same volume of water and 100 ml of ethyl acetate in a separating funnel. The shaking was repeated several times after separating the ethyl acetate layer each time. The combined ethyl acetate layers were evaporated to give a concentrate.

The thin-layer chromatogram of the concentrate under the following conditions is shown in FIG. 1 of the accompanying drawing: solvent, hexane/ether/formic acid = 130/80/20 (by volume); coloration, heating for 5 seconds after spraying 10% (by weight) sulfuric acid.

In FIG. 1, a to i are the chromatograms of the authentic samples in which a denotes salazinic acid, b stictic acid, c protocetraric acid, d fumarprotocetraric acid, e squamatic acid, f norstictic acid, g thiophanic acid, h usnic acid and i calycine, respectively.

Comparison of the chromatogram numbered 1 with those of authentic samples proves the presence of usnic acid, salazinic acid, protocetraric acid and norstictic acid.

EXAMPLE 2

A small piece with an area of about 0.5 cm$^2$ was cut from thallus of Parmelia subramigera (Parmelaceae, Lecanorales) collected at Hirakata-shi. The procedure in Example 1 was repeated using this small piece to give a concentrate, chromatogram of which is shown in FIG. 1. (The culture is deposited under Deposition No. NP L-20.)

Comparison of the chromatogram numbered 2 with those of authentic samples proves the presence of usnic acid, protocetraric acid and fumarprotocetraric acid.

EXAMPLE 3

A small piece with an area of about 0.5 cm$^2$ was cut from thallus of Pertusaria flavicans (Pertusariaceae, Lecanorales) collected at Hirakata-shi. The procedure in Example 1 was repeated using this small piece to give a concentrate, the chromatogram of which is shown in FIG. 1. (The culture is deposited under Deposition No. NP L-19.)

Comparison of the chromatogram numbered 3 with those of authentic samples proves the presence of thiophanic acid and sticnic acid.

EXAMPLE 4

The procedures in Example 1 was repeated except that the podetium of Cladonia pseudomacilenta (Cladoniaceae, Lecanorales) was used in place of thallus of Usnea rubescens. A chromatogram of the obtained concentrate is shown in FIG. 1. (The culture is deposited under Deposition No. NP L-16.)

Comparison of the chromatogram numbered 4 with those of authentic samples proves the presence of usnic acid and squamatic acid.

EXAMPLE 5

The procedures in Example 1 was repeated except that a small piece with an area of about 0.5 cm$^2$ cut from Pseudocyphellaria aurata (Stictaceae, Lecanorales) collected at Kyoto-shi was used in place of thallus of Usnea rubescens. A chromatogram of the obtained concentrate is shown in FIG. 1. (The culture is deposited under Deposition No. NP L-2.)

Comparison of the chromatogram numbered 5 with those of authentic samples proves the presence of calycine, stictic acid and norstictic acid.

EXAMPLE 6 to 29

Using the lichenous plants shown below, tissue culture was carried out in the same manner similar as in Example 1 to give undifferentiated symbionts, which were then cultured in liquid medium. Various compounds reported in the literature were proved in the culture.

| Example | Name | Location | Deposition No. |
|---|---|---|---|
| 6 | Parmelia calvulifera | Kyoto-shi | NP L-1 |
| 7 | Parmelia squarrosa | Kyoto-shi | NP L-3 |
| 8 | Parmelia caperata | Kyoto-shi | NP L-4 |
| 9 | Menegazzia terebrata | Kyoto-shi | NP L-5 |
| 10 | Parmelia tinctorum | Kyoto-shi | NP L-6 |
| 11 | Parmelia entotheiochroa | Kyoto-shi | NP L-7 |
| 12 | Usnea dorogawaensis | Kyoto-shi | NP L-8 |
| 13 | Ramalina subgeniculata | Kyoto-shi | NP L-9 |
| 14 | Ramalina yasudae | Kyoto-shi | NP L-11 |
| 15 | Usnea rubicunda | Kyoto-shi | NP L-12 |
| 16 | Lobaria orientalis | Toyama-ken | NP L-13 |
| 17 | Alectoria ochroleuca | Nagano-ken | NP L-14 |
| 18 | Usnea aciculifera | Kyoto-shi | NP L-15 |
| 19 | Anaptychia microphylla | Kyoto-shi | NP L-17 |
| 20 | Pyxine endochrysina | Hirakata-shi | NP L-18 |
| 21 | Lobaria discolor | Shiga-ken | NP L-22 |
| 22 | Parmelia rudecta | Kyoto-shi | NP L-23 |
| 23 | Cladonia rangiferina | Kyoto-shi | NP L-24 |
| 24 | Peltigera canina | Kyoto-shi | NP L-25 |
| 25 | Evernia esorediosa | Furano-shi | NP L-45 |
| 26 | Usnea diffracta | Furano-shi | NP L-42 |
| 27 | Cetraria juniperina | Furano-shi | NP L-53 |
| 28 | Evernia prunastri | Furano-shi | NP L-47 |
| 29 | Usnea longissima | Furano-shi | NP L-39 |

EXAMPLE 30

About 1 g (wet weight) of the undifferentiated symbionts obtained in Example 1 was transplanted in culture medium with the same composition as in Example 1 and incubated at 25° C. in light of 2,000 lux continuously passing sterile air containing 1% of gaseous carbon dioxide at a rate of 5 ml/min. After 2 months of culture, there was obtained about 7 g (wet weight) of undifferentiated symbionts.

EXAMPLE 31

A small piece with an area of about 0.5 cm$^2$ was cut from thallus of Parmelia caperata (Parmeliaceae, Lecanorales) collected at Kyoto-shi and used for explant. The explant was placed aseptically on the same synthetic culture medium as in Example 1 and incubated at 25° C. in light of 1,000 lux. After about 3 weeks of culture, there were formed green-colored undifferentiated symbionts.

About 1 g (wet weight) of the symbionts obtained above were transplanted in culture medium with the same composition as in Example 1 and incubated at 25° C. in light of 1,000 lux continuously passing sterile air containing 1.5% of gaseous carbon dioxide at a rate of 5 ml/min. After 2 months of culture, there was obtained about 6 g (wet weight) of undifferentiated symbionts.

EXAMPLE 32

A small piece with a length of about 1 cm was cut from thallus of Ramalina subgeniculata (Osneaceae, Lecanorales) collected at Kyoto-shi and used for explant. The explant was placed aseptically on the same synthetic culture medium as in Example 1 and incubated at 25° C. in light of 2,000 lux. After about 3 weeks of culture, there were formed green-colored undifferentiated symbionts.

About 1 g (wet weight) of the symbionts obtained above were transplanted in culture medium with the same composition as in Example 1 and incubated at 25° C. in light of 2,000 lux continuously passing sterile air containing 1% of gaseous carbon dioxide at a rate of 5 ml/min. After 2 months of culture, there was obtained about 7 g (wet weight) of undifferentiated symbionts.

EXAMPLE 33

A small piece with an area of about 0.5 cm$^2$ was cut from thallus of Pyxine endochrysina (Physciaceae, Lecanorales) collected at Hirakata-shi and used for explant. The explant was placed aseptically on the same synthetic culture medium as in Example 1 and incubated at 25° C. in light of 1,000 lux. After about 3 weeks of culture, there were formed green-colored undifferentiated symbionts.

About 1 g (wet weight) of the symbionts obtained above were transplanted in culture medium with the same composition as in Example 1 and incubated at 25° C. in light of 1,000 lux continuously passing sterile air containing 1.5% of gaseous carbon dioxide at a rate of 5 ml/min. After 2 months of culture, there was obtained about 6 g (wet weight) of undifferentited symbionts.

EXAMPLE 34

The undifferentiated symbionts (3 g) obtained in Example 1 were suspended in a sterilized 3% sodium alginate solution (10 ml), which was added dropwise to a sterilized CaCl$_2$ solution (0.05 M) to form a gel. The gel was chopped into divisions of immobilized lichens.

EXAMPLE 35

A small piece with an area of about 0.5 cm$^2$ was cut from thallus of Parmeria caperata (Parmeriaceae, Lecanorales) collected at Kyoto-shi and cultured in the same manner as in Example 1.

The obtained undifferentiated symbiont (3 g) was mixed with a 0.9% collagen fibril solution (80 ml) and formed into a film by casting. The film, after drying, was dipped in a 1% glutaraldehyde solution to give a bridged structure of immobilized lichen film.

EXAMPLE 36

A small piece with an area of about 0.5 cm$^2$ was cut from thallus of Pertusaria flavicans (Pertusariaceae, Lecanorales) collected at Hirakata-shi and cultured in the same manner as in Example 1.

The obtained undifferentiated symbionts (4 g) were mixed with acrylamide (4.5 g), N,N'-methylenebisacrylamide (0.05 g) and physiological saline solution to form a suspension. A mixture of the suspension, 5% aqueous methylaminopropionitrile (0.5 g) and 2.5% aqueous potassium persulfate solution (1 g) was kept at 10° C. for 30 minutes to form a gel. The gel was crushed into particles of immobilized lichens.

EXAMPLE 37

A small piece with an area of about 0.5 cm$^2$ was cut from thallus of Pixine endochrysina (Physiaceae, Lecanorales) collected at Hirakata-shi was cultured in the same manner as in Example 1.

The obtained undifferentiated symbionts (5 g) of Pixine endochrysina were suspended in a phosphate buffer (10 ml) of pH 7.5. Buffered ion-exchange resins (Diaion HP-10, 10 ml) of pH 7.0 were added to the suspension.

The mixture was shaken overnight at 30° C. with a velocity of 220 rpm, decanted, washed several times with phosphate buffer by decantation in order to remove unreacted symbionts and wring to give immobilized lichen particles.

EXAMPLE 38

A piece with an area of about 0.5 cm² was cut from Pseudocyphellaria aurata (Stictaceae, Lecanorales) (having no apothecium) collected at Kyoto-shi, washed well with water and added to an enzymatic solution (10 ml) on a clean bench. The enzymatic solution was prepared by dissolving "Dricellase" (manufactured by Kyowa Hokko) (4 % w/v), 0.7 M mannitol, 20mM morpholinethanesulfonic acid and 5 mM magnesium chloride in distilled water, subjecting the resultant solution to centrifugation at 2500 rpm and subjecting the supernatant to sterile filtration by the use of a millipore filter of 0.22 micron. The said enzymatic solution comprising the piece of Pseudocyphellaria aurata was shaken with 70 c/s and 5 cm wide at 25° C. for 6 hours. Then, the resultant mixture was filtered through a filter of 150 microns. The filtrate was further filtered through a filter of 62 microns. The cell blocks on the filter were washed with sterile water several times. One hundred cell blocks were collected, and each of them was placed on a medium in a test tube. The medium was prepared by sterilizing an aqueous composition comprising malt extract (Difco)(2% w/v), yeast extract (Difco)(0.2% w/v) and agar (2% w/v) in a conventional manner and admitting every 5 ml of the sterilized composition into each test tube.

Cultivation was carried out at 25° C. in a dark place. After about one month, the cell block was grown up so that the cell culture could be well observed by naked eye. The non-contamination rate (i.e. number of non-contaminated cultures/number of total cultures) was 41%, and the survival rate (i.e. number of survival cultures/number of total cultures) was 100%. The survival cultures comprised the cultures consisting of fungus cells only, the cultures consisting of algal cells only and the cultures consisting of both fungus cells and algal cells.

EXAMPLE 39

A piece with a length of about 1 cm was cut from Usnea rubescens (Usneaceae, Locanorales) (having no apothecium) collected at Kyoto-shi, washed well with water and crushed on a mortar in a clean bench. The crushed material was filtered through a filter of 500 microns. The filtrate was further filtered through a filter of 150 microns. The cell blocks on the filter were washed with sterile water several times, and each of the cell blocks was placed on the medium as in Example 38 and cultivated. After about one month, the cell block was grown up so that the cell culture could be well observed by naked eye. The rate of non-contamination was 30%, and the rate of survival was 100%. The survival cultures comprised the cultures consisting of fungus cells only (deposited at American Type Culture Collection under Accession Number ATCC 20668), the cultures consisting of algal cells only (deposited at American Type Culture Collection under Accession Number ATCC 20667) and the cultures consisting of both fungus cells and algal cells.

EXAMPLE 40

A piece with an area of about 0.5 cm² was cut from Pertusaria flavicans (Pertusariaceae, Lecanorales) (having no apothecium) collected at Hirakata-shi, washed well with sterile water and crushed in a mortar. As in Example 39, the crushed material was treated, and the obtained cell blocks were each placed on a medium having the same composition as in Example 38 but comprising additionally coatside (0.1% w/v). Cultivation was carried out as in Example 38. After about one month, the cell block was grown up so that the cell culture could be observed by naked eye. The rate of non-contamination was 69%, and the rate of survival was 97%. The survival cultures comprised the cultures consisting of algal cells only.

EXAMPLE 41

A piece with an area of about 0.5 cm² was cut from Parmelia subramigera (Parmelaceae, Lecanorales) (having no apothecium) collected at Hirakata-shi, washed with sterile water and cut finely with a sterile knife in a clean bench. The finely cut material was dispersed in sterile water and filtered as in Example 39. The obtained cell blocks were each placed on a medium having the same composition as in Example 38 but comprising additionally salicillin (50 ppm) and kanamycin (50 ppm). Cultivation was carried out as in Example 38. After about one month, the cell block was grown up so that the cell culture could be observed by naked eye. The rate of non-contamination was 23%, and the rate of survival was 77%. The survival cultures comprised the cultures consisting of algal cells only.

EXAMPLE 42

The cell cultures of Usnea rubescens (50 mg) as obtained in Example 39 were crushed in a mortar in a clean bench, and the resulting cell blocks were each placed in the same medium as in Example 38. Cultivation was carried out as in Example 38. After about one month, the cell block was grown up so that the cell culture could be observed by naked eye. The rate of survival was 100%. The survival cultures comprised three kinds of the cultures as in Example 39.

EXAMPLES 43 to 70

In the same manner as in Example 38, pieces of lichenous plants as shown below were treated, and the obtained cell blocks were cultivated. As the result, there were obtained the cell cultures of thee kinds, i.e. the ones consisting of fungus cells only, the ones consisting of algal cells only and the ones consisting of both fungus cells and algal cells.

| Example | Name | Location |
| --- | --- | --- |
| 43 | Parmelia calvulifera | Kyoto-shi |
| 44 | Parmelia squarrosa | Kyoto-shi |
| 45 | Parmelia caperata | Kyoto-shi |
| 46 | Menegazzia terebrata | Kyoto-shi |
| 47 | Parmelia tinctorum | Kyoto-shi |
| 48 | Parmelia entotheiohroa | Kyoto-shi |
| 49 | Usnea dorogawaensis | Kyoto-shi |
| 50 | Ramalina subgeniculata | Kyoto-shi |
| 51 | Ramalina yasudae | Kyoto-shi |
| 52 | Usnea rubicunda | Kyoto-shi |
| 53 | Lobaria orientalis | Toyama-ken |
| 54 | Alectoria ochroleuca | Nagano-ken |
| 55 | Usnea aciculifera | Kyoto-shi |
| 56 | Anatychia microphylla | Kyoto-shi |

-continued

| Example | Name | Location |
| --- | --- | --- |
| 57 | Pyxine endochrysina | Hirakata-shi |
| 58 | Lobaria discolor | Shiga-ken |
| 59 | Parmelia rudecta | Kyoto-shi |
| 60 | Cladonia rangiferina | Kyoto-shi |
| 61 | Peltiera canina | Kyoto-shi |
| 62 | Evernia esorediosa | Furano-shi |
| 63 | Usnea diffracta | Furano-shi |
| 64 | Cetraraia juniperina | Furano-shi |
| 65 | Evernia prunastri | Furano-shi |
| 66 | Usnea longissima | Furano-shi |
| 67 | Ramalina boninensis | Tokyo-to |
| 68 | Ramalina pacifica | Tokyo-to |
| 69 | Umbilicaria esculenta | Hiroshima-ken |
| 70 | Umbilicaria kisovana | Hiroshima-ken |

What is claimed is:

1. A block of cells of lichen flora consisting of at least one fungus cell and at least one algal cell in symbiotic association, said block of cells having no contamination with any fungus cells not in symbiotic association with said algal cell and having no contamination with any bacterial cells, and wherein the number of the cells in the block is at least two and the maximum size of the block is not more than 1 mm, said block being produced by a process which comprises micronizing at least a portion of a body of lichen flora containing contaminating fungus cells and bacterial cells in an aqueous medium so as to leave at least two of the cells and having a maximum size of not more than 1 mm, subjecting the thus micronized product to filtration with at least one filter capable of retaining the said block and passing any other cell(s) than those of the said lichen flora and any contaminating fungus cells and bacterial cells therethrough and collecting the said block retained on the filter.

2. A method for obtaining a block of cells of lichen flora consisting of at least one fungus cell and at least one algal cell in symbiotic association, said block of cells having no contamination with any fungus cells any bacterial cells, and wherein the number of the cells in the block is at least two and the maximum size of the block is not more than 1 mm, which comprises micronizing at least a portion of a body of lichen flora containing contaminating fungus cells and bacterial cells in an aqueous medium so as to leave at least two of the cells and having a maximum size of not more than 1 mm, subjecting the thus micronized product to filtration with at least one filter capable of retaining the said block and passing any other cell than those of the said lichen flora and any contaminating bacterial cells and fungus cells therethrough and collecting the said block retained on the filter.

3. The method according to claim 2, wherein the micronization is achieved by any physical, chemical or physical and chemical procedure.

* * * * *